United States Patent [19]
Drake et al.

[11] Patent Number: 6,093,536
[45] Date of Patent: Jul. 25, 2000

[54] WOOD'S ANOMALY ASSAY TECHNIQUE AND KIT

[75] Inventors: Rosemary Ann Lucy Drake, Royston; Craig George Sawyer, St. Neots; Grenville Arthur Robinson, London, all of United Kingdom

[73] Assignee: Ares-Serono Research & Development Limited Partnership, Boston, Mass.

[21] Appl. No.: 07/146,246

[22] Filed: Jan. 20, 1988

[30] Foreign Application Priority Data

Jan. 21, 1987 [GB] United Kingdom ............... 8701293
Nov. 4, 1987 [GB] United Kingdom ............... 8725797

[51] Int. Cl.$^7$ ............................................. C12Q 1/68
[52] U.S. Cl. ...................... 435/6; 356/354; 435/7.1; 435/7.2; 435/7.92; 435/7.94; 436/501; 436/518; 436/524; 436/532
[58] Field of Search .......................... 356/128, 354; 436/518, 501, 524, 535, 532, 805, 808; 435/7, 287, 810, 7.1, 7.2, 7.6, 7.9, 7.92, 7.93, 7.94, 7.95, 6

[56] References Cited

U.S. PATENT DOCUMENTS

| | | | |
|---|---|---|---|
| 4,454,233 | 6/1984 | Wang ............................. | 436/525 |
| 4,521,522 | 6/1985 | Lundstrom et al. .............. | 436/525 |
| 4,626,513 | 12/1986 | Burton ............................ | 436/518 |
| 4,647,544 | 3/1987 | Nicoli et al. .................... | 436/519 |
| 4,703,018 | 10/1987 | Craig et al. ..................... | 436/805 |

FOREIGN PATENT DOCUMENTS

| | | |
|---|---|---|
| 0112721 | 4/1984 | European Pat. Off. . |
| 0167335 | 1/1986 | European Pat. Off. . |
| 0171148 | 2/1986 | European Pat. Off. . |
| 0178083 | 4/1986 | European Pat. Off. . |
| 2173895 | 10/1986 | United Kingdom . |

OTHER PUBLICATIONS

"Surface Plasmon Resonance For Gas Detection And Biosensing*" by Bo Liedberg et al., Sensors and Actuators, 4 (1983) pp. 299–304.

Biosensors, Fundamentals and Applications (Ed. A. Turner, Oxford Univ. Press, New York, NY, 1987) pp. 655, 661–663, and 666.

Tiefenthaler et al. (1984) Optics Letters, vol. 10, No. 4, p. 137.

Greestein et al. (1967) Technical Papers, vol. XIII, Annual Conference, Society of Plastic Engineers, Inc., Detroit, Mich., p. 1121.

Monoclonal Antibodies and Developments in Immunoassay, (Eds. Albertini et al., Elsevier/North Holland Bioch. Press, NY, NY, 1981) pp. 3–21.

*Primary Examiner*—Ardin H. Marschel
*Attorney, Agent, or Firm*—Ostrolenk, Faber, Gerb & Soffen, LLP

[57] ABSTRACT

A method of assaying for a ligand in a sample which includes incubating, simultaneously or in any desired sequence,    a) the sample b) a reagent X and c) a reagent Y immobilised on the surface of an optical structure capable of exhibiting surface plasmon resonance, one of reagents X and Y is a specific binding partner to said ligand and the other of reagents X and Y is either a ligand analogue or a specific binding partner to said ligand, reagent X being such, that any formation of a direct or indirect complex between reagents X and Y results in an optical surface having an appreciably enhanced optical thickness as compared to the optical thickness of the optical surface which would prevail in the absence of reagent X, which method includes the step of determining whether and, if desired, the extent to which and/or rate at which the surface plasmon resonance effect exhibited by the optical structure is altered by said complex formation.

14 Claims, 7 Drawing Sheets

DEVELOPING SOLUTION

Plot of shift in the Wood's anomaly (nm) versus concentration of influenza virus (particles per ml), from $10^8$ to $10^{12}$.

- △ Virus plus antibody A plus antibody B on grating blocked with BSA
- ● Virus plus antibody A on grating blocked with BSA
- × Virus plus BSA coated strip

WOOD'S ANOMALY ASSAY TECHNIQUE AND KIT

BACKGROUND

This invention relates to assay techniques and to means for putting such techniques into effect. In particular it relates to an improved assay technique providing enhanced sensitivity and specificity.

The properties of simple optical structures have been known for many years and structures such as, for example, diffraction gratings have widespread use, not only as tools for understanding and analysing the wave properties of electromagnetic radiation but also, more recently, as sensors for detecting chemical, biochemical or biological species in a sample.

EP-0112721 describes the preparation, and use as biosensors, of optical structures having a pre-formed relief profile coated with a material (hereinafter called "specific binding partner") capable of binding with the species to be assayed (hereinafter called "ligand") to form a complex. The optical properties of such structures are altered as a result of complex formation between the ligand and the specific binding partner and this phenomenon can consequently form the basis of an assay system.

The change in optical properties of the structures described above is a function of the mass or bulk of the bound ligands, their dielectric properties and their optical characteristics such as refractive index and transparency. Hence, although the basic concept of utilising perturbed optical properties such as surface plasmon resonance (SPR) effects to form a sensor is valid, the practical applications of such methods have hitherto been limited because of poor sensitivity to small, low molecular weight ligands. This poor sensitivity precludes accurate measurement, at clinical concentrations, of low molecular weight ligands, for example with a molecular weight of less than 10,000 daltons.

A further difficulty experienced with the practical application of the technique described in EP-0112721 is that of poor specificity. This arises at two distinct stages of the assay procedure:

i) Non-specific binding of sample components to the surface of the optical structure. This can give rise to false positive results and inaccurate quantification of the perturbation of optical properties which arise as a result of specific ligand binding.

ii) The use of only a single recognition step, i.e. the use of only one specific binding partner for the ligand to be analysed, can reduce specificity. Thus, where a ligand is present in a sample both as intact units and as fragments, e.g. parathyroid hormone, the use of only a single recognition step may result in both forms being bound when it may be desirable to measure only the intact, and hence biochemically active, molecules.

We have now devised an improved assay technique which can overcome the sensitivity disadvantages of the prior art and in some embodiments may also result in improved specificity.

SUMMARY OF THE INVENTION

This invention relates to a method of assaying for a. ligand in a sample by incubating the sample, a reagent X and a reagent Y immobilized directly or indirectly on the surface of an optical structure capable of exhibiting surface plasmin resonance, one of X and Y comprising a specific binding partner to the ligand and the other comprising either a ligand analog or a specific binding partner to the ligand, reagent X being such that any formation of a direct or indirect complex between reagents X and Y results in an optical surface having an appreciably enhanced optical thickness as compared to the optical thickness of the optical surface which would prevail in the absence of reagent X, the method including the step of determining whether and if desired the extent to which and/or the rate at which the surface plasmin resonance effect exhibited is altered during the assay. The invention also relates to a kit for carrying out the method.

DESCRIPTION OF THE INVENTION

Thus, the present invention provides a method of assaying for a ligand in a sample which comprises incubating, simultaneously or in any desired sequence, a) the sample
b) a reagent X and
c) a reagent Y immobilised directly or indirectly on the surface of an optical structure capable of exhibiting surface plasmon resonance, one of reagents X and Y comprising a specific binding partner to said ligand and the other of reagents X and Y comprising either a ligand analogue or a specific binding partner to said ligand, reagent X being such, that any formation of a direct or indirect complex between reagents X and Y results in an optical surface having an appreciably enhanced optical thickness as compared to the optical thickness of the optical surface which would prevail in the absence of reagent X, which method includes the step of determining whether and, if desired, the extent to which and/or rate at which the surface plasmon resonance effect exhibited by the optical structure is altered by said complex formation. Where one of reagents X and Y comprises a ligand analogue and the other of reagents X and Y comprises a specific binding partner to the ligand, complex formation between reagents X and Y may occur directly. Alternatively, where both reagents X and Y comprise specific binding partners to the ligand, complex formation between reagents X and Y indirectly via the ligand, if present in the sample, may occur.

It is to be understood that reagent Y may be immobilised on the surface of the optical structure either directly or indirectly. For example, when reagent Y is an antibody, indirect immobilisation may be effected by means of an anti-species antibody to reagent Y which is itself bound to the surface of the optical structure.

The term "optical structure capable of exhibiting surface plasmon resonance" as used herein defines any structure which is optically active with respect to radiation over a predetermined band of wavelengths and which exhibits surface plasmon resonance effects which are critically dependent on the surface characteristics of the structure. Preferably the structure has a pre-formed surface relief profile and the use of metallised diffraction gratings is particularly preferred. However, other optical structures which exhibit surface plasmon resonance effects e.g. metal coated prisms are also of use in the method according to the invention.

The surface plasmon resonance (SPR) properties of such optical structures may be observed by exposing the structure to electromagnetic radiation, preferably monochromatic radiation, more particularly polarised light, and monitoring the reflected or transmitted radiation. The use of a diffraction grating and incident radiation in the form of light polarised in a plane transverse to the lines of the grating is particularly preferred.

The term "ligand analogue" as used herein refers to a species capable of complexing with the same binding site of the same specific binding partner as the ligand under assay, and includes inter alia within its scope a known quantity of the ligand under assay.

The term "optical thickness" as used herein defines a composite optical property of a material which is a function of both its physical thickness and its refractive index. It has been found that the SPR effects of an optical structure, for example a diffraction grating, to which a ligand-specific binding partner complex is bound are critically dependent on the optical thickness of the bound complex. Thus, the change in the SPR effects of an optical structure induced by the formation of a ligand-specific binding partner complex may be enhanced by increasing the optical thickness of the bound layer without increasing the ligand concentration.

The term "optical surface" is not necessarily used herein to denote simply the surface of the optical structure itself but where appropriate in the context includes any material (for example immobilised complex) present on the surface of the optical structure.

The enhancement in optical thickness of the optical surface resulting from complex formation is achieved by utilising as reagent X a reagent which appreciably increases either the physical size of the bound complex or the refractive index of the bound complex. Typically, the increase in complex size will be of the order of 100 nm or greater or the refractive index will be increased to 1.5–2.0. As mentioned above, reagent X comprises either a ligand analogue or a specific binding partner to the ligand under assay. However, reagent X must be such that any complex formation (direct or indirect) between reagents X and Y (leading to bound complex on the surface of the optical structure) results in an optical surface of appreciably enhanced optical thickness as described above. Where the ligand analogue or specific binding partner is not of itself sufficiently large to achieve this, the reagent x will be a ligand analogue or specific binding partner "labelled" by linkage to an optical thickness enhancing entity, e.g. polystyrene latex, a virus, a microorganism, ferritin, or a protein such as a second specific binding partner.

The sensitivity of the assay method according to the invention may be still further enhanced by the use of et reagent x which incorporates a suitable particle of high refractive index ($\mu$) e.g. glass beads $\mu$>2.0, in particular lithium niobate glass with $\mu$>2.2. Such reagents increase both the size and refractive index of the bound complex and the concomitant increase in the optical thickness of the optical surface allows a still further improvement in the sensitivity of the assay method according to the invention.

Methods of assay in accordance with the invention include methods wherein i) reagent Y is a ligand analogue and reagent X is a specific binding partner to the ligand, optionally linked to an optical thickness enhancing entity;

ii) reagent Y is a specific binding partner to the ligand and reagent X is a ligand analogue linked to an optical thickness enhancing entity; or iii) reagent Y is a specific binding partner to the ligand and reagent X is a specific binding partner (identical to or different from reagent Y) to the ligand, optionally linked to an optical thickness enhancing entity.

Hence, reagent X may comprise any suitably large ligand analogue or specific binding partner to the ligand. Thus, for example, if the ligand is an antigen reagent X may be a relatively large antibody thereto, optionally bound to one or more further entities which further increase the optical thickness enhancement properties of reagent X. Alternatively, reagent X may be an entity having, at the surface thereof, at least one antigenic determinant analogous to the sample antigen (ligand) such that competition for specific binding sites provided by the immobilised reagent Y can take place between the sample antigen (ligand) and reagent X.

The use, as reagent X, of a second specific binding partner to the ligand, optionally linked to one or more other optical thickness enhancing entities or particles as described above, will not only improve the sensitivity of the method according to the invention but will also improve its specificity in the manner described above. Thus, where the ligand to be assayed is an antigen or an antibody, the use of an antibody or antigen specific thereto, optionally linked to one or more other entities e.g. glass beads, as the optical thickness enhancing reagent X, is particularly preferred.

The method according to the invention extends the range of ligands which may be assayed using SPR effect perturbation techniques from viruses with a molecular weight of $2 \times 10^8$ daltons or higher down to, and including, ligands having a low molecular weight e.g. 200–500 daltons such as steroids, drugs etc. Hence, the assay techniques of this type are no longer limited by the physical size of the ligand itself.

The modified procedure according to the invention may be applied to a "competition-type" assay. Thus, for example, the optical thickness of the optical surface may be increased using as reagent X a ligand analogue linked to a comparatively large "label" particle, such as latex. Introducing reagent X together with the sample containing the ligand under assay to the surface of an optical structure bearing a specific binding partner to the ligand allows reagent X and the ligand to compete for the binding sites provided by reagent Y. Complex between reagents X and Y will be formed in a quantity inversely proportional to the concentration of ligand in the sample.

Alternatively, reagent X can consist of a large "label" particle coated with a specific binding partner to the ligand to be assayed for and this reagent X can be incubated with the sample and the optical structure coated with immobilised ligand analogue (reagent Y) such that the amount of complex formed between reagents X and Y is again inversely proportional to the concentration of ligand in the sample.

In another embodiment of the invention, large "label" entities may be used in a so-called sandwich assay. In this case, the ligand is capable of binding both with a specific binding partner immobilised on the surface of an optical structure (reagent Y) and with a second specific binding partner, which may be the same or different, carried on the surface of an optical thickness enhancing entity (reagent X). If present, the sample ligand indirectly links reagent X and reagent Y resulting in a complex between all three.

In a further embodiment of the invention the enhanced optical thickness of the bound layer is achieved by allowing large aggregates to form following complex formation between reagents X and Y.

According to another aspect of the invention there is provided a kit for carrying out a method of assay as described herein which comprises a reagent X as defined above and an optical structure on the surface of which is immobilised a reagent Y as defined above.

The enhanced optical thickness of the optical structure due to complex formation between reagents X and Y is detected by monitoring the SPR effect. In the preferred embodiment of the invention where the optical structure is a metallised diffraction grating, this involves directing light, polarised in a plane transverse to the lines of the grating, onto the grating surface and detecting the change in surface plasmon resonance effects caused by complex formation. Thus, the angle of incidence at which there is a sudden dip in the magnitude of reflected or diffracted light may be measured. This sudden dip is caused by light energy being coupled into the surface of the grating and causing surface plasmon resonance to occur at a particular angle which depends on the optical characteristics of the grating surface, and in particular on the optical thickness of the optical surface. Alternatively, the angle of incidence may be held constant and the wavelength of the irradiating light varied to detect the altered SPR characteristics of the surface.

The invention will be particularly described hereinafter (except for Example 3) with reference to an antibody or an antigen as the ligand. However the invention is not to be taken as being limited to assays of antibodies or antigens. Examples of ligands which may be assayed by the method of the invention are given in Table 1 below, together with an indication of a suitable specific binding partner in each instance.

TABLE 1

| Ligand | Specific Binding Partner |
| --- | --- |
| antigen | specific antibody |
| antibody | antigen |
| hormone | hormone receptor |
| hormone receptor | hormone |
| polynucleotide strand | complementary polynucleotide strand |
| avidin | biotin |
| biotin | avidin |
| protein A | immunoglobulin |
| immunoglobulin | protein A |
| enzyme | enzyme cofactor (substrate) or inhibitor |
| enzyme cofactor (substrate) or inhibitor | enzyme |
| lectins | specific carbohydrate |
| specific carbohydrate of lectins | lectins |

The method of the invention has very broad applicability but in particular may be used to assay: hormones, including peptide hormones (e.g. thyroid stimulating hormone (TSH), luteinising hormone (LH), human chorionic gonadotrophin (hCG), follicle stimulating hormone (FSH), insulin and prolactin) or non-peptide hormones (.e.g steroid hormones such as cortisol, estradiol, progesterone and testosterone, or thyroid hormones such as thyroxine (T4) and triiodothyronine), proteins (e.g. carcinoembryonic antigen (CEA) and alphafetoprotein (AFP)), drugs (e.g. digoxin), sugars, toxins, vitamins, viruses such as influenza, parainfluenza, adeno-, hepatitis, respiratory and AIDS viruses, or microorganisms.

It will be understood that the term "antibody" used herein includes within its scope:
  (a) any of the various classes or sub-classes of immunoglobulin, e.g. IgG, IgM, derived from any of the animals conventionally used, e.g. sheep, rabbits, goats or mice,
  (b) monoclonal antibodies,
  (c) intact molecules or "fragments" of antibodies, monoclonal or polyclonal, the fragments being those which contain the binding region of the antibody, i.e. fragments devoid of the Fc portion (e.g. Fab, Fab', F(ab')$_2$) or the so-called "half-molecule" fragments obtained by reductive cleavage of the disulphide bonds connecting the heavy chain components in the intact antibody.

The method of preparation of fragments of antibodies is well known in the art and will not be described herein.

The term "antigen" as used herein will be understood to include both permanently antigenic species (for example, proteins, bacteria, bacterial fragments, cells, cell fragments and viruses) and haptens which may be rendered antigenic under suitable conditions.

The following general assay formats illustrate particular embodiments of the invention.

Aggregation Technique

Antibodies are typically divalent and large antigens such as proteins are often multivalent. It is therefore possible for a single antibody to bind to two antigens, which may be the same or different, simultaneously or for several antibodies to be bound to a single antigen. Thus, when antigen and antibody are mixed in solution the direct antigen-antibody reaction initially leads to the formation of small complexes. When the number of antibody binding sites is close to the number of antigen binding sites extensive cross linking between antibody and antigen can occur which causes large aggregates to develop.

Figure 1:
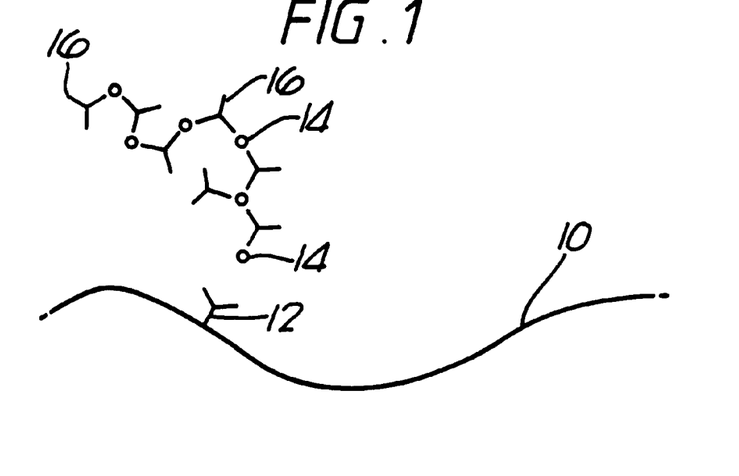
FIG. 1 shows diagramatically a diffraction grating having immobilized antibody thereon and sample containing the species to be assayed.

FIG. 1 shows diagrammatically the surface of a diffraction grating 10 on which is immobilised an antibody 12 (reagent Y) specific for the species to be assayed, an antigen 14. The sample containing the antigen 14, reagent X in the form of a specific antibody 16 which may bind to the antigen 14 (and which may or may not be the same as antibody 12) and the grating 10 are then brought into contact, simultaneously or in any desired sequence, such that the large antibody-antigen aggregate formed is bound to the surface of the grating via antibody 12. The number of antibody/antigen complexes formed on the grating can be detected by the altered SPR properties of the surface.

The time course of formation of aggregates in solution is rapid but additional reagents such as polyethylene glycol may be used to enhance immuno-precipitation. Using this method to form aggregates at the surface of a suitable diffraction grating in order to enhance the SPR effect does not therefore result in longer incubation times or add further processing steps to the diffraction grating-based assay. For example, reagent X 16 (specific antibody) could be added to the sample and the aggregates allowed to form for a few minutes before the thus enhanced sample is applied to the test diffraction grating which bears immobilised antibody 12 specific for sample antigen 14 on its surface (reagent Y).

Alternatively, aggregates can be formed directly at the surface of the test diffraction grating and the alteration of the SPR effects of the surface can be monitored with time as aggregate formation proceeds. A still further variation on this type of assay system is based on conventional immunoassay systems wherein aggregate formation is inhibited, for example, by small molecules such as drugs.

Particulate Labels

The following examples utilise a reagent X comprising a ligand analogue or a specific binding partner to the ligand linked to one or more particles of defined size, chemical and optical properties. The particle itself is the dominant entity measured directly by the SPR effect rather than the sample ligand analogue or specific binding partner to the ligand.

Suitable particulate labels comprise materials suitable for the formation of small particles e.g. 100 nm diameter, are relatively transparent to allow the incident light to pass through the bound particle, and preferably have a high refractive index, more preferably higher than 2.0, such that surface plasmon resonance effects are enhanced. The surface of the particle should be of suitable material to permit immobilisation of the required ligand analogue or specific binding partner e.g. protein antigen or antibody, thereto. Synthetic particles may comprise for example polymeric material such as latex, glass, in particular lithium niobate glass, colloidal silver or gold, metal oxide or ferritin and naturally-occurring particles include cells, for example microorganisms, viruses, starch granules and pollen grains.

There are several assay formats in which such a particulate label may be used and which are based upon conventional immunoassay techniques, well known in the art, and which are not themselves discussed herein.

a) Competition assay format

Small molecules such as drugs and hormones may be measured in a number of different ways using a competitive assay format.

Figure 2:
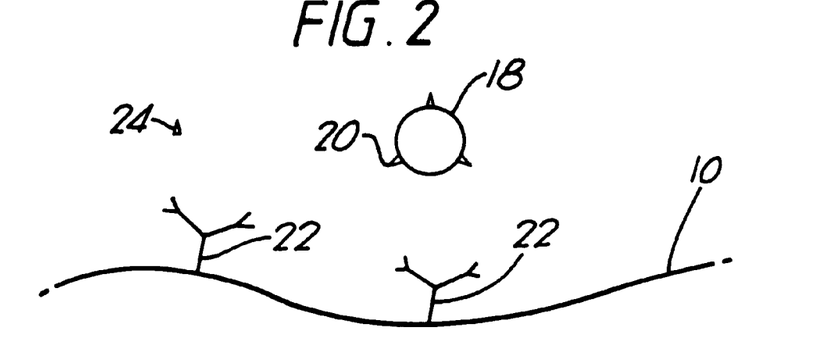
FIG. 2 shows diagrammatically a competition assay format.

Referring to FIG. 2, reagent X comprises a label particle 18 bearing antigen 20 (which may or may not be the same as sample antigen 24) on its surface. Reagent Y comprises a specific antibody 22 immobilised onto the surface of a diffraction grating 10. When sample antigen 24 and reagent X are incubated with the grating test strip, competition for binding to the antibody 22 takes place between sample antigen 24 and antigen 20 bound to particle 18. The amount of particle 18 bound to the surface of the test grating 10 will be in inverse proportion to the concentration of the sample antigen 24, thus allowing measurement of the sample antigen 24.

Figure 3:
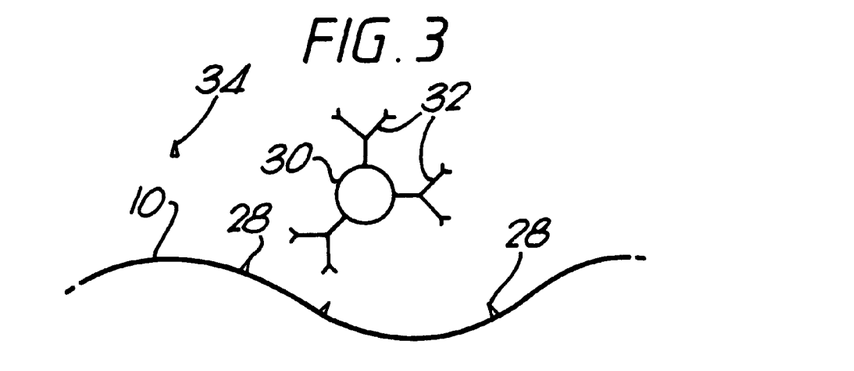
FIG. 3 shows diagrammatically an alternative competition assay format.

FIG. 3 shows an alternative competition assay. In this case, a diffraction grating 10 carries reagent Y which comprises an immobilised antigen 28 (which may or may not be the same as sample antigen 34) and reagent X comprises a label particle 30 carrying antibody 32 specific to the sample antigen 34 and the immobilised antigen 28. The sample antigen 34 and the immobilised antigen 28 compete for binding sites on the antibody 32, so that the amount of reagent X bound to the surface of the test grating 10 will be in inverse proportion to the concentration of the sample antigen 34, thus allowing measurement of the sample antigen 34.

b) Sandwich assay format

This format is applicable to antigens which are sufficiently large to bear on their surface more than one site which can be recognised and bound by an antibody. Such antigens are able to bind to at least two antibodies simultaneously and therefore are able to bridge between the antibodies.

Figure 4:
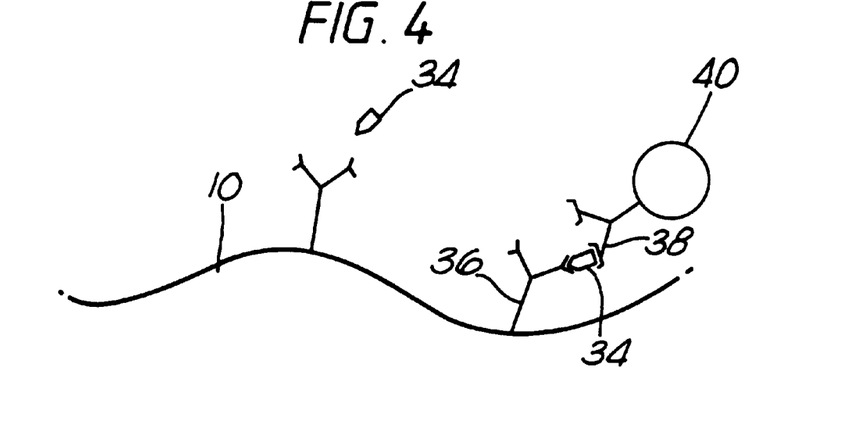
FIG. 4 shows diagrammatically a sandwich assay format.

Referring to FIG. 4, in the case of a bivalent sample antigen 34, a bridge is formed between the antibody 36 bound to the surface of the test grating 10 (reagent Y) and another antibody 38 (which may or may not be the same as antibody 36) bound to the surface of a label particle 40 which forms reagent X. The amount of bound reagent X is then determined thus allowing measurement of the sample antigen 34. Increasing the sample antigen concentration causes an increase in the amount of bound reagent X.

Figure 5:
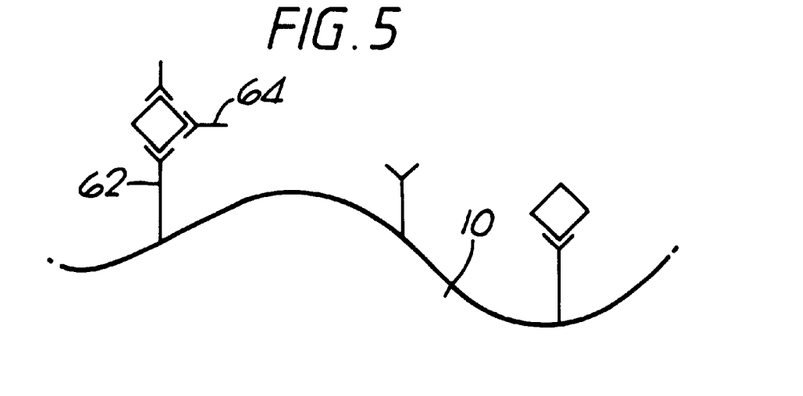
FIG. 5 shows diagrammatically an alternative type of sandwich assay format.

FIG. 5 shows an alternative type of sandwich assay where a multivalent sample antigen is to be determined. The multivalent sample antigen 60 forms a bridge between the antibody 62 bound to the surface of the test grating 10 (reagent Y) and at least one reagent X comprising an antibody 64 (which may or may not be the same as antibody 62). The effective size of the bound sample antigen 60 is thus increased, allowing more sensitive measurement of the sample antigen 60.

c) Agglutination assay format

A previously described embodiment of the invention illustrates how antibody-antigen-antibody complex formation in a sandwich-type immunoassay can enhance the sensitivity and specificity of the assay. Particles may be used to enhance further the sensitivity of such assays. Assays may employ direct agglutination or agglutination inhibition formats. The latter are used for measuring small molecules in a competition assay format as previously described.

It is proposed that the large particulate aggregates which form in the presence of sample antigen or antibody are specifically captured onto the surface of a diffraction grating by means of a specific binding partner (reagent Y). In one example, reagent X in the form of labelled particles would be added to the sample and ligand, if present in the sample, will cause agglutination to occur. Addition of the particle-enhanced sample to the test grating will allow capture of the aggregates onto the surface where they may be measured by SPR effects. Alternatively, the contacting of reagent X, sample and reagent Y attached to a diffraction grating may be simultaneous rather than sequential and the rate of formation of the aggregate on the surface of the grating could be measured to determine the ligand under assay.

Figure 6:
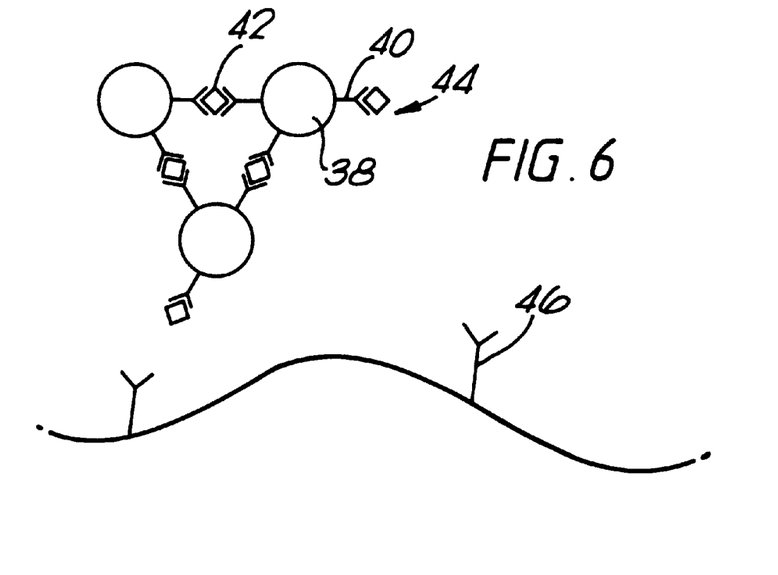
FIG. 6 shows diagrammatically an aglutenation assay format.

FIG. 6 shows diagrammatically an agglutination assay format. An inert support particle 38 carries antibodies 40 which bind with the sample antigen 42. The resulting large aggregate 44 is bound to the surface of the diffraction grating 10 by antibody 46 (which may or may not be the same as antibody 40) immobilised on the surface of the grating 10. The antibody 46 binds to the antigen 42 of the large aggregate and the amount of sample antigen 42 can then be measured.

Complex Precipitation Assay

Carbohydrate polymers such as alginate or chitosan can exist in different forms, as soluble polymers or as insoluble particles. The transition from one form to the other can be effected by the addition of certain ions e.g. $Ca^{++}$ causes soluble alginate to precipitate. It is proposed that this effect could be used to enhance the SPR assay described herein. For example, reagent X may comprise a long chain polymer labelled with a ligand. This reagent can compete with sample ligand for binding to the specific antibody on the grating surface (reagent Y). Once bound, a developing solution to precipitate the bound polymer is added before measurement.

Figure 7A:
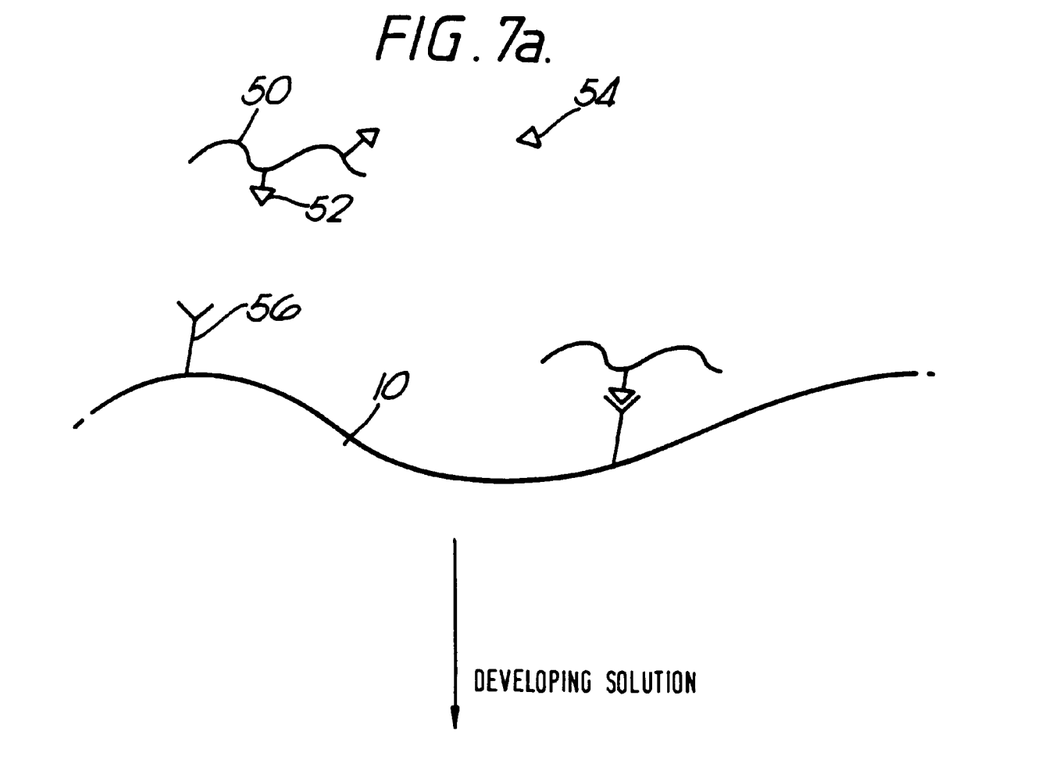
FIGS. 7a and 7b show diagrammatically a complex precipitation assay.
Figure 7B:
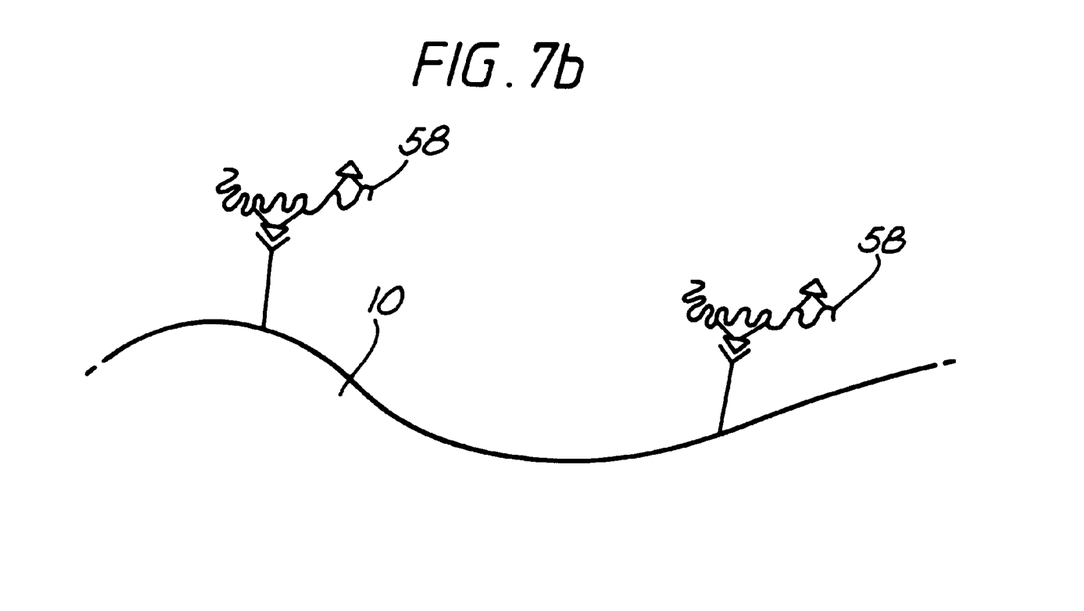

For example, referring to FIGS. 7a and 7b, a long chain polymer 50 is labelled with antigen 52 (which may or may not be the same as sample antigen 54). This labelled antigen competes with "free" sample antigen 54 for binding sites on antibody 56 immobilised on the grating surface. A developing solution is then added to precipitate the bound labelled antigen (58, FIG. 7*b*). The amount of labelled antigen 58 bound and precipitated onto the surface of the grating 10 is inversely proportional to the concentration of sample antigen 54.

Similarly, sandwich format assays could be developed using such precipitatable polymers.

The following non-limiting examples illustrate assays carried out in accordance with the invention.

EXAMPLE 1

The use of a Second Antibody as a Label in the Detection of Influenza a Virus

Preparation of Starting Antibodies

1. Anti-influenza Monoclonal Antibodies

Monoclonal antibodies were obtained from mouse ascites fluid by the process reported by Milstein and Kohler in Nature 256, 495–497 (1975). Antibodies from individual hybridoma cell lines were screened to identify those producing antibody to discrete antigenic determinants of Influenza A virus. Those antibodies having the highest affinities for Influenza A virus, strain X-31, were selected for use in the assay. The capture antibody (antibody A) was used at 50 µg/ml in phosphate buffered saline (PBS) containing 0.1% bovine serum albumin (BSA) (Sigma Chemical Co. Ltd., England) and the label antibody (antibody B) at 50 µg/ml in PBS.

2. Preparation of Influenza A Virus Strain X-31

Influenza A virus, strain X-31, was grown in eggs by standard techniques (see, for example, pages 593–594 of "Diagnostic Procedures For Viral, Rickettsial and Chlamydia Infections, 5th Edition" by E. H. Lennette and N. J. Schmidt published by the American Public Health Association, 1979). The virus, after precipitation with polyethylene glycol, was purified by sucrose density gradient centrifugation. Prior to use the virus was diluted in PBS containing 0.1% BSA.

3. Preparation of Metallised Diffraction Gratings

Diffraction gratings (633 nm pitch, 35 nm depth) were fabricated in polycarbonate by injection moulding. The gratings were then coated with a 10 nm thick layer of chromium followed by a 100 nm thick layer of gold. Both metal layers were deposited by thermal evaporation under vacuum.

4. Apparatus for Measurement of the Surface Plasmon Resonance (SPR) Phenomenon

Figure 8:
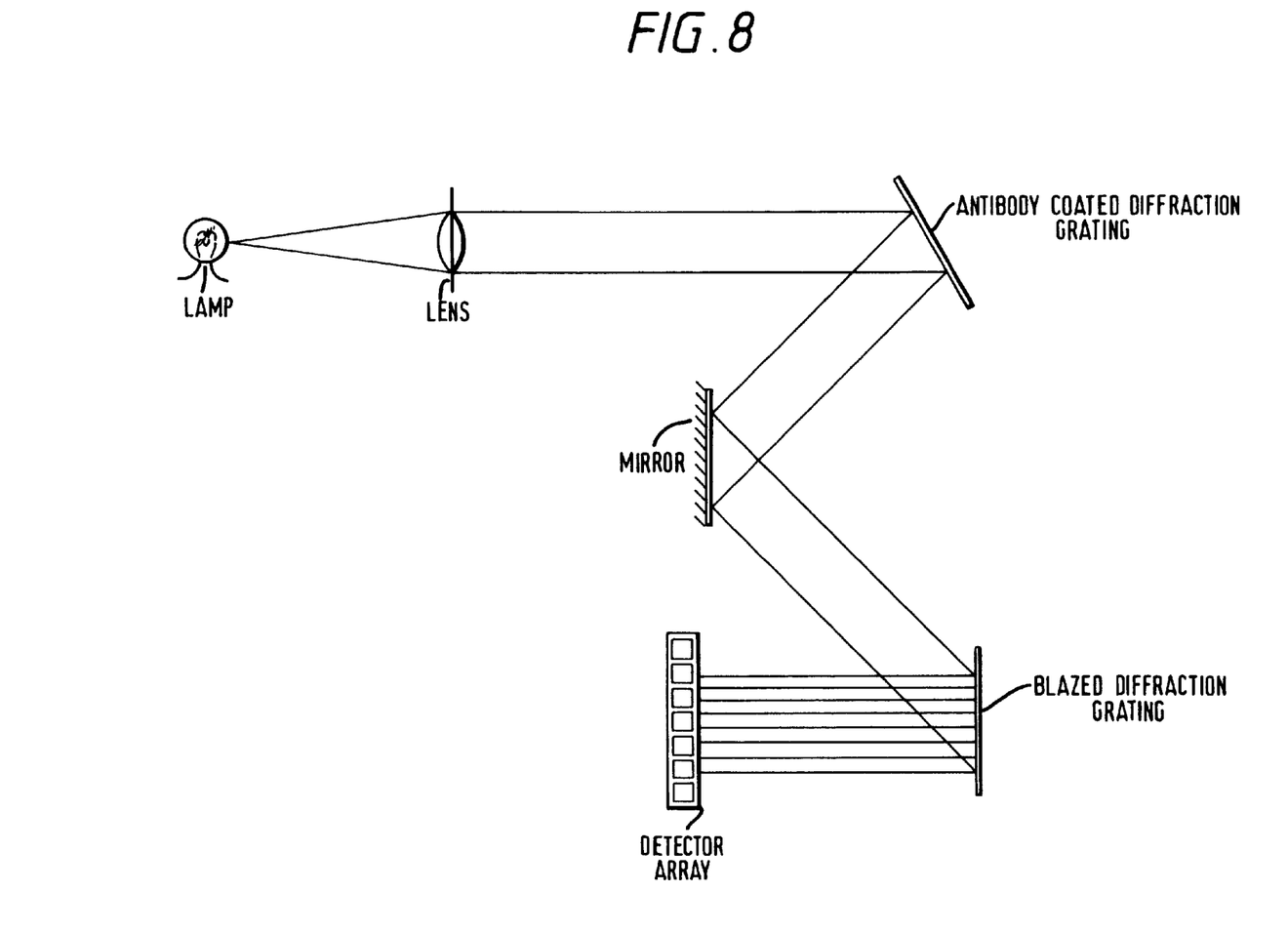
FIG. 8 shows diagrammatically an optical system which can be used in accordance with the invention.

Surface plasmon resonance was generated using an instrument shown in FIG. 8. The instrument consists of a collimated beam of plane polarised white light which illuminates the antibody coated diffraction grating. The light is then directed via a mirror from the antibody coated diffraction grating onto a blazed diffraction grating where the light is broken into its component wavelengths and thence focussed onto a 256 pixel photodiode array which measures the light intensity at specific wavelengths.

Experimental Procedure For Detecting Influenza a Virus

Clean, gold coated diffraction gratings were read in the instrument and the wavelength of the Wood's anomaly (the minimum in reflected light intensity which results from the generation of surface plasmon resonance on a diffraction grating) recorded. 250 µl aliquots of antibody A or PBS containing 0.1% BSA (to produce control gratings) were pipetted onto the surface of the gratings in order to immobilise the antibody. The strips were incubated for 60 minutes at 37° C. in a moist atmosphere. After washing the strips with PBS, 250 µl aliquots of dilutions of either virus or diluent were applied to the strip and incubated at 37° C. for 2 hours in a moist atmosphere with slight agitation (85 rpm). After a further wash with PBS, 250 µl aliquots of either antibody B or diluent were applied to the strip and incubated for 1 hour at 37° C. in a moist atmosphere with slight agitation (85 rpm). The strips were washed with PBS followed by distilled water. After air drying the position of the Wood's anomaly for each strip was read.

Figure 9:
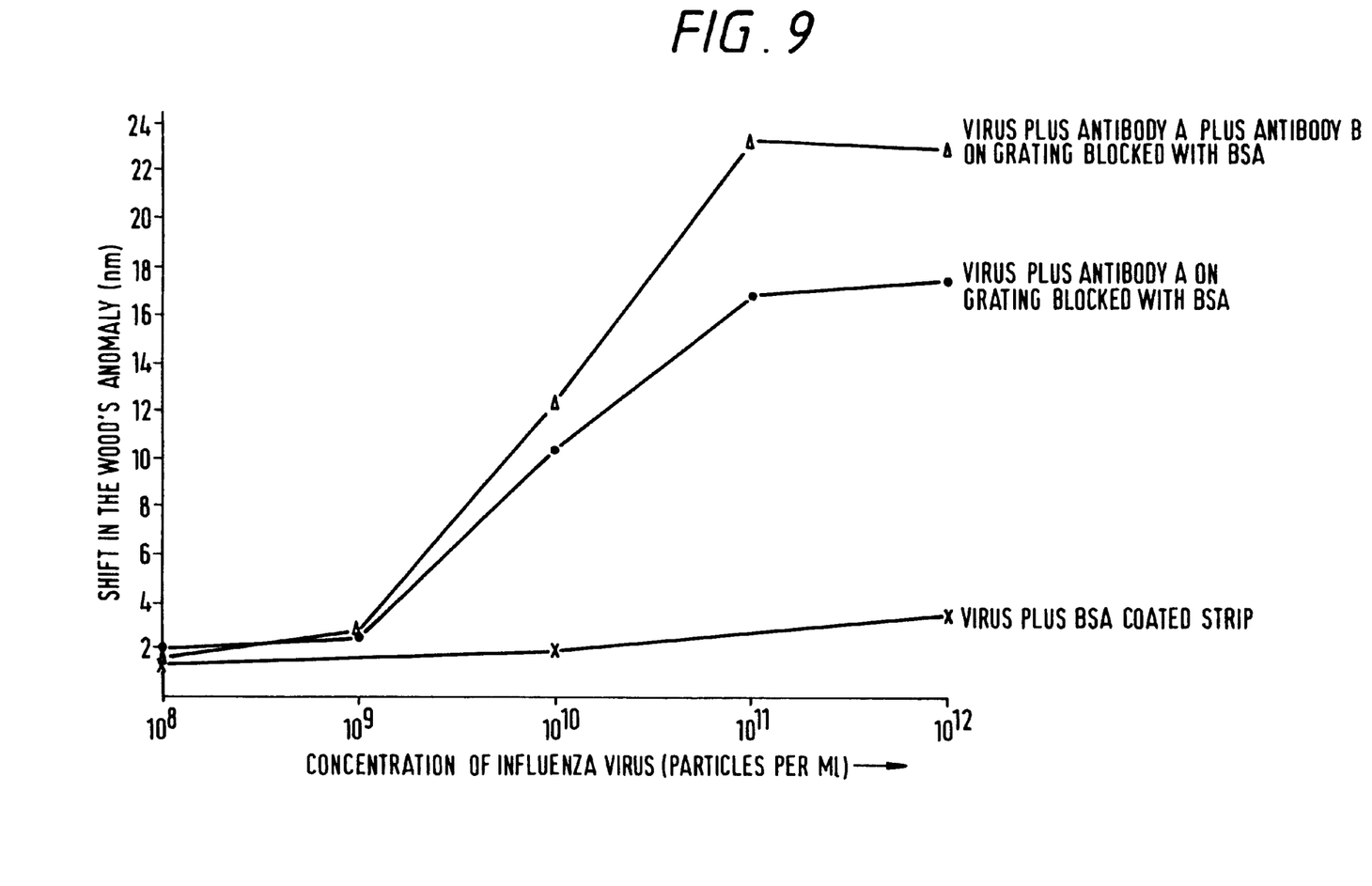
FIG. 9 is a graph showing displacement in the Wood's, anomaly.

FIG. 9 shows the displacement in the Wood's anomaly caused by the influenza virus binding to the immunologically active diffraction grating and the enhanced signal obtained when the second antibody was bound to the influenza virus particle.

EXAMPLE 2

The Use of Influenza Virus as a Label in an Assay to Detect Antibodies Against Influenza Virus in Human Serum Preparation of Starting Materials 1. Preparation of Viral Haemagglutinin Influenza A virus (strain X-31) was grown and purified as described in Example 1. Haemagglutinin was extracted from the virus using the bromelain method as described by Brand and Skehel in Nature New Biology Volume 238 (1972), p145–147.

2. Human Anti-influenza Sera

Human sera which were both positive and negative by haemagglutination inhibition assay for influenza A virus, strain X-31, were obtained from the National Institute for Medical Research, Mill Hill, London. The sera were tested in the assay as dilutions of ¹/₂₀, ¹/₁₆₀ and ¹/₁₂₈₀ diluted in PBS containing 0.1% BSA.

3. Preparation of Influenza A Virus

Influenza A virus was prepared as described in Example 1.

4. Preparation of Metallised Diffraction Gratings

Metallised diffraction gratings were prepared as described in Example 1.

5. Apparatus for the Measurement of the Surface Plasmon Resonance (SPR) Phenomena The apparatus was as described in Example 1.

Experimental Procedure For Detecting Antibodies Against Influenza a Virus in Human Serum Clean, gold coated diffraction gratings were read in the instrument and the wavelength of the Wood's anomaly (the minimum in reflected light intensity which results from the generation of surface plasmon resonance on a diffraction grating) recorded. 250 µl aliquots of haemagglutinin (50 µg/ml in PBS) were spread over the diffraction gratings and incubated for 37° C. for 1 hour in a moist atmosphere. After washing with PBS, the strips were incubated with 1% BSA in PBS for 1 hour at 37° C. in a moist atmosphere. After a further wash with PBS, 250 µl aliquots of either human sera or diluent were applied to the diffraction gratings and incubated for 2 hours at 37° C. in a moist atmosphere with slight agitation (85 rpm). Following a PBS wash, 250 µl aliquots of either influenza virus or diluent were applied to the diffraction gratings and incubated for 2 hours at 37° C. in a moist atmosphere with slight agitation (85 rpm). The gratings were then washed with PBS followed by distilled water and air dried prior to measuring the position of the Wood's anomaly for each strip.

Figure 10:
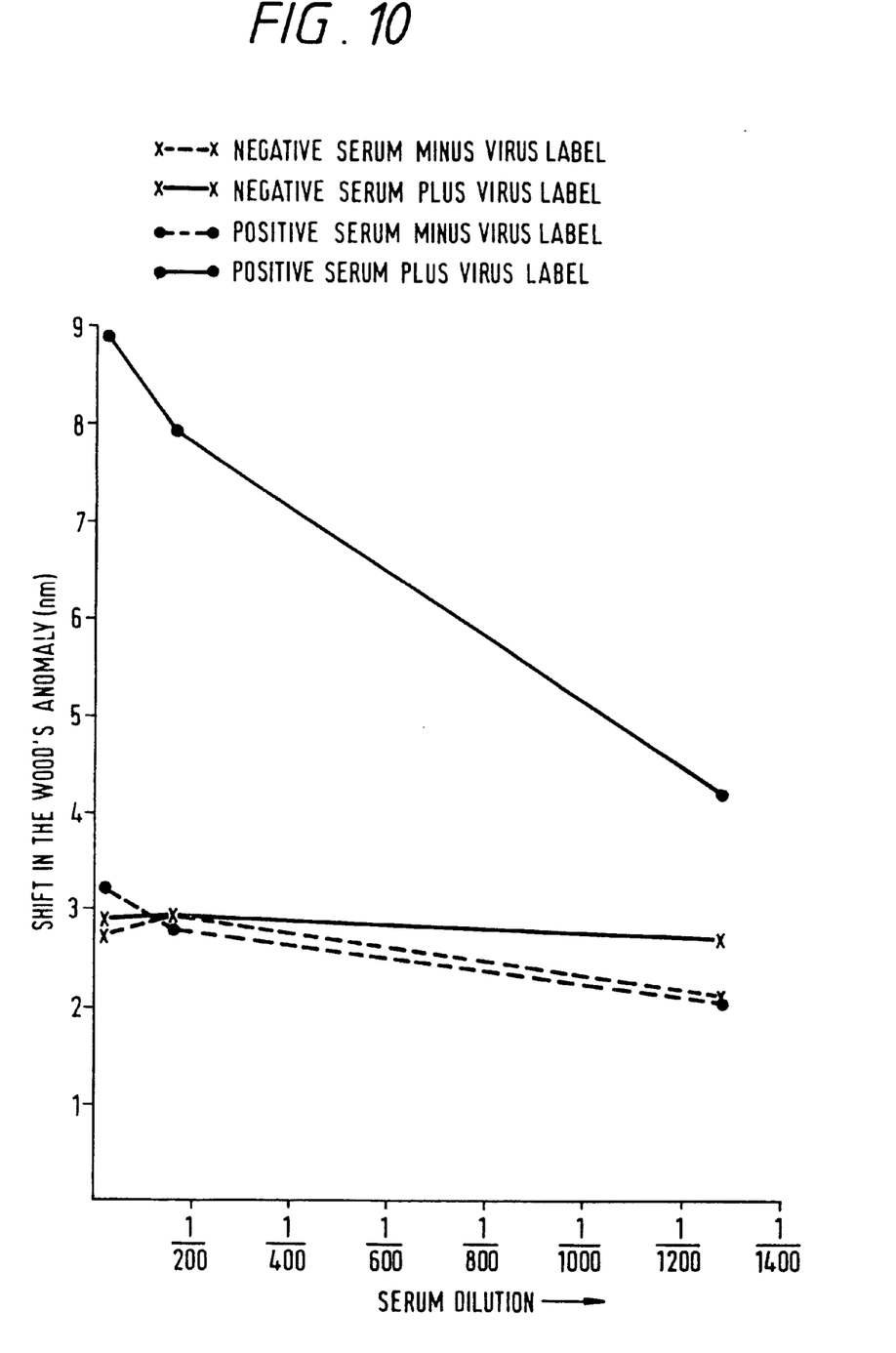
FIG. 10 is a graph showing shifts in the position of the Wood's anomaly.
Figure 11:
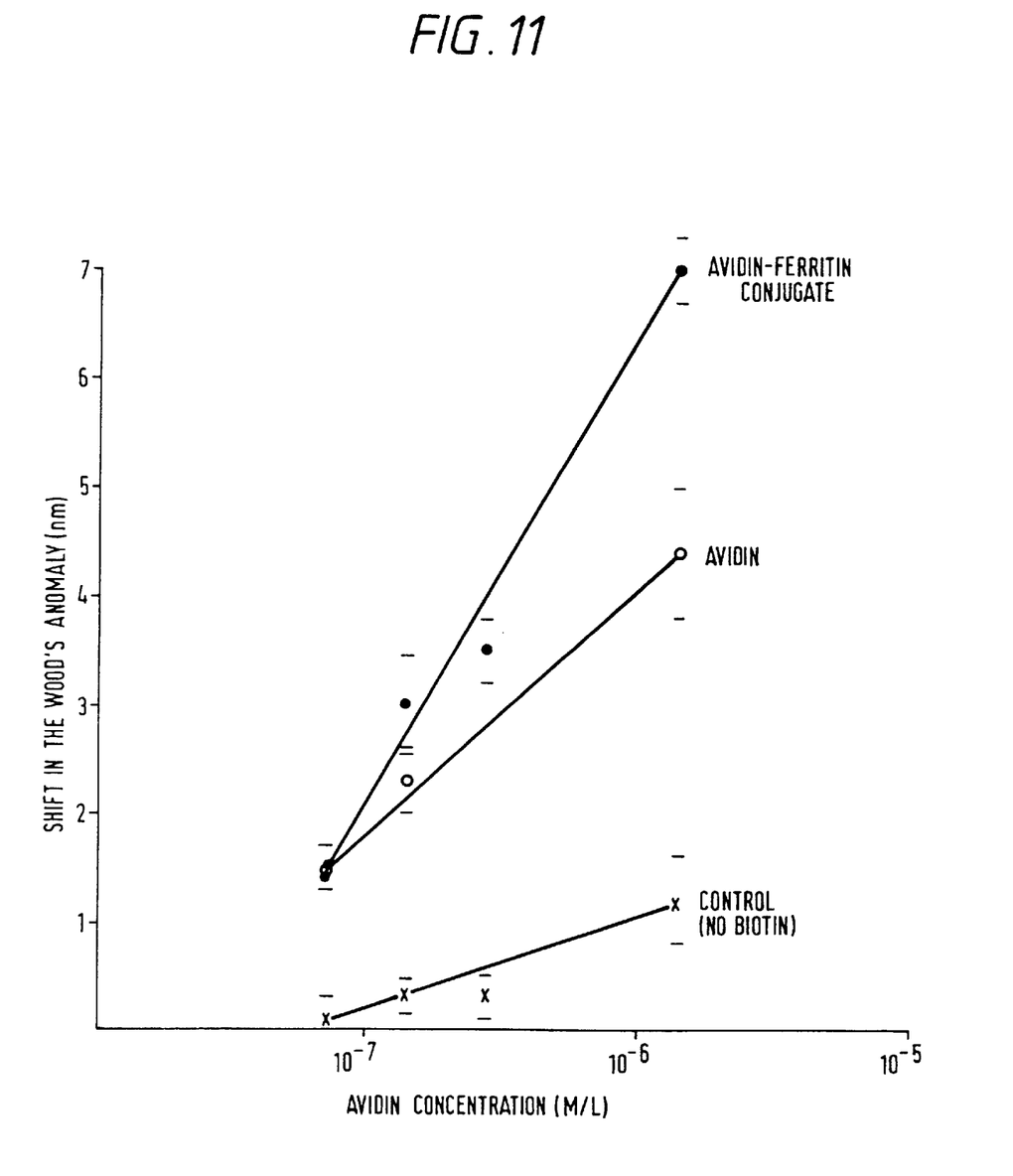
FIG. 11 shows shifts in the positions of Wood's anomaly upon the binding of avidin and avidin-ferritin to biotin coated diffraction gratings.

FIG. 10 shows the shifts in the position of the Wood's anomaly, measured in nanometers, which were obtained by binding different dilutions of positive and negative sera to the diffraction gratings in the presence and absence of the virus particle label.

EXAMPLE 3

The Use of Ferritin as a Label in an Assay to Detect Avidin

Preparation of Starting Materials

1. Preparation of Biochemical Reagents

Biotin conjugated to the enzyme peroxidase via a spacer molecule, diaminodipropylamine (DAPA), avidin and a conjugate of ferritin labelled avidin were obtained from Sigma Chemical Company, London.

The biotin-peroxidase conjugate was made up to 0.068 mg/ml in 0.05 molar carbonate/bicarbonate buffer, pH 9.6, avidin-ferritin and avidin were dissolved in 0.05 molar phosphate buffer pH 7.4.

2. Preparation of Metallised Diffraction Gratings

The metallised diffraction gratings were made as described in Example 1.

3. Apparatus for the Measurement of the Surface Plasmon Resonance (SPR) Phenomenon The apparatus was as described in Example 1.

Experimental Technique 0.4 ml of the biotin solution was added to each gold coated diffraction grating and incubated for 1½ hours at 37° C. After washing with carbonate/bicarbonate buffer, the gratings were incubated with 0.4 ml of 0.1% BSA in carbonate/bicarbonate buffer for 2 hours at 37° C. After a further wash with carbonate/bicarbonate buffer, 0.4 ml of serially diluted avidin or avidin-ferritin solution was added to the gratings and incubated for 2 hours at 37° C. The gratings were then washed with phosphate buffer followed by distilled water prior to air drying and measuring the position of the Wood's anomaly.

FIG. 11 shows the shifts in the positions of the Wood's anomaly, measured in nanometers, upon the binding of avidin and avidin-ferritin to the biotin coated diffraction gratings. The increase in signal due to the presence of the ferritin is clearly observed.

We claim:

1. A method of assaying for a ligand in a sample which method comprises the steps of:

incubating, simultaneously or in any desired sequence, a) the sample containing the ligand;

b) a reagent X; and c) a reagent Y immobilized directly or indirectly on the surface of an optical structure capable of exhibiting surface plasmon resonance, one of reagents X and Y comprising a specific binding partner to the ligand and the other of reagents X and Y comprising either a ligand analogue or a specific binding partner to the ligand, reagent X being such that any formation of a direct or indirect complex between reagents X and Y results in an optical surface having an appreciably enhanced optical thickness as compared to the optical thickness of the optical surface which would prevail in the absence of reagent X, which method includes the step of determining whether and, if desired, the extent to which and/or rate at which the wavelength of the Wood's Anomaly exhibited by the optical structure is altered during the assay.

2. A method as claimed in claim 1 wherein reagent X increases the size of any complex formed by at least 100 nm.

3. A method as claimed in claim 1 wherein reagent X increases the refractive index of any layer of complex formed to 1.5–2.0.

4. A method as claimed in claim 1 wherein reagent X comprises a particle having a refractive index of at least 2.0.

5. A method as claimed in claim 1 wherein the optical structure is a diffraction grating.

6. A method as claimed in claim 1 wherein reagent X comprises a polymer labelled with a ligand.

7. A method as claimed in claim 1, wherein the ligand has a molecular weight of about 200 to about 500.

8. A method as claimed in claim 1, wherein the ligand is a steroid or a drug.

9. A kit for carrying out a method of assay which comprises a reagent X, as defined in claim 1, and an optical structure capable of exhibiting surface plasmon resonance on the surface of which is immobilised a reagent Y, as defined in claim 1.

10. A kit as claimed in claim 9 wherein reagent Y is a ligand analogue and reagent X is a specific binding partner to the ligand, linked to an optical thickness enhancing entity.

11. A kit as claimed in claim 9 wherein reagent Y is a specific binding partner to the ligand and reagent X is a ligand analogue linked to an optical thickness enhancing entity.

12. A kit as claimed in claim 9 wherein reagent Y is a specific binding partner to the ligand and reagent X is a specific binding partner to the ligand, linked to an optical thickness enhancing entity.

13. A kit as claimed in claim 9 wherein reagent X comprises a particle having a refractive index of at least 2.0.

14. A kit as claimed in claim 9 wherein reagent X comprises a polymer labelled with a ligand.

* * * * *

UNITED STATES PATENT AND TRADEMARK OFFICE
CERTIFICATE OF CORRECTION

PATENT NO : 6,093,536
DATED : July 25, 2000
INVENTOR(S) : DRAKE, Rosemary A.L. et al.

It is certified that error appears in the above identified patent and that said Letters Patent are hereby corrected as shown below.

In the heading of the patent, under "[73] Assignee:", for "Ares-Serono Research & Development Limited Partnership, Boston, Mass." read --Applied Research Systems ARS Holding N.V., Netherlands--

Signed and Sealed this

First Day of May, 2001

Attest:

NICHOLAS P. GODICI

*Attesting Officer*   *Acting Director of the United States Patent and Trademark Office*